United States Patent [19]

Sasagawa et al.

[11] Patent Number: 4,508,655
[45] Date of Patent: Apr. 2, 1985

[54] METAL COMPLEXES OF HALOGEN-SUBSTITUTED O-BENZENEDITHIOLS

[75] Inventors: Katsuyoshi Sasagawa; Masao Imai, both of Yokohama, Japan

[73] Assignee: Mitsui Toatsu Chemicals, Inc., Tokyo, Japan

[21] Appl. No.: 448,331

[22] Filed: Dec. 9, 1982

[30] Foreign Application Priority Data

Dec. 16, 1981 [JP] Japan ................. 56-201574
Dec. 16, 1981 [JP] Japan ................. 56-201575

[51] Int. Cl.³ .................. C07F 15/00; C07F 15/04
[52] U.S. Cl. .................. 260/429 R; 260/429 J; 260/429 K; 260/439 R; 525/17
[58] Field of Search .......... 260/429 K, 429 J, 429 R, 260/439 R

[56] References Cited

U.S. PATENT DOCUMENTS 2,737,529 3/1956 Bradley ............... 260/439 R X
2,842,578 7/1958 Pikl ................... 260/439 R X

OTHER PUBLICATIONS

Chemical Abstracts, 71(4): 18366z (1966).
Chemical Abstracts, 71(4): 18386f (1969).
Chemical Abstracts, 71(22): 105864d (1969).

*Primary Examiner*—Helen M. S. Sneed
*Attorney, Agent, or Firm*—Kane, Dalsimer, Kane, Sullivan and Kurucz

[57] ABSTRACT

Metal complexes of halogen-substituted o-benzenedithiols of the general formula:

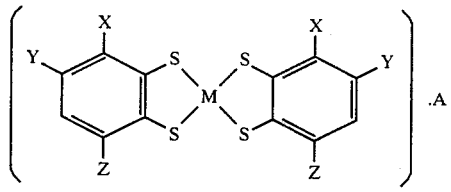

wherein X represents a chlorine or bromine atom, Y and Z represent each a hydrogen or chlorine atom when X is a chlorine atom or they represent each a hydrogen or bromine atom when X is a bromine atom, M represents a nickel, palladium or platinum atom, and A represents a quaternary ammonium group, are provided.

These metal complexes have a high compatibility with resins and are useful as near infrared absorbers. Halogen-substituted o-benzenedithiols of the formula:

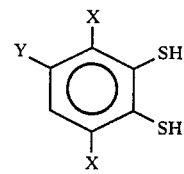

wherein X, Y and Z have the same meaning as above; used as starting materials for the above metal complexes are also new compounds.

2 Claims, No Drawings

METAL COMPLEXES OF HALOGEN-SUBSTITUTED O-BENZENEDITHIOLS

BACKGROUND OF THE INVENTION

The present invention relates to new metal complexes of halogen-substituted o-benzenedithiols, new halogen-substituted o-benzenedithiols used as starting materials therefor, processes for producing the same and plastic compositions containing said metal complexes as near-infrared absorbers.

Known o-benzenedithiols such as benzene-1,2-dithiol, 1-methylbenzene-3,4-dithiol, 1,2-dimethylbenzene-4,5-dithiol and 1,2,3,4-tetramethylbenzene-5,6-dithiol have a high metal chelating capacity. It has been known that metal complexes of o-benzenedithiols obtained by reacting the thiols with metal ions, such as bis(1,2-dithiophenolato) nickel-tetra-n-butylammonium, bis(1-methyl-3,4-dithiophenolato)nickel-tetra-n-butylammonium, bis (1,2,3,4-tetramethyl-5,6-dithiophenolato)nickel-tetra-n-butylammonium and bis(1,2,3,4-tetrachloro-5,6-dithiophenolato)nickel-tetra-n-butylammonium exhibit a specific absorption spectrum in a near-infrared zone ["Toluol-3,4-dithiol und verwandte 1,2-Dithiolene als Chelatbildner för Metalle" Monatschefte für Chemie, Vol. 102, pp. 308–320 (1971) and "Characterization and Electronic Structures of Metal Complexes Containing Benzene-1,2-dithiolate and Related Ligands" Journal of the American Chemical Society, Vol. 88, pp. 4870–4875 (1966)]. These metal complexes having excellent thermal stability and weather resistance (Japanese Patent Laid-Open No. 135551/1981) are used as important near-infrared absorbers. Investigations are made on the use of them by incorporating them as near-infrared absorbers in plastic films or plates or by applying polymer solutions containing them to bases to form films for agricultural use for the selective absorption of the sunlight as well as sunglasses, welder's glasses, aircraft windows and TV filters so as to reduce the glare of the light or fatigue of eyeballs. Further, recently, investigations are made of the use of the metal complexes for producing optical filters for the compensation of wavelength dependence of the sensitivity of optical transducer elements such as photodiodes and light-emitting diodes. These metal complexes are used also as important absorbers and regenerators of laser beams for semiconductor laser beam recording, i.e. laser heat mode recording, since the near-infrared absorption zone of them coincides with the oscillation wavelength of the semiconductor lasers.

However, known metal complexes of o-benzenedithiols excluding those derived from 1,2,3,4-tetrachlorobenzene-5,6-dithiol (Japanese Patent Laid-Open No. 135463/1981) are quite expensive, since they are produced by complicated, multi-step synthesis reactions. Therefore, the uses of them have been limited.

On the contrary, since the above-mentioned tetrachlorobenzenedithiol can be produced economically advantageously and a metal complex derived therefrom has an excellent near-infrared absorbing capacity, this complex has been used practically. However, if resins in the form of films or plates containing a large amount of this complex as near-infrared absorber are used, the metal complex of tetrachlorobenzenedithiol is crystallized out of the resin. For example, if 20 wt. % or more of the metal complex is incorporated in an acrylic resin, this phenomenon occurs particularly remarkably. Therefore, this complex is unsuitable if it should be contained in a high concentration in a resin, particularly when a high near-infrared absorbing capacity is required of a thin film containing a high concentration of the complex prepared according to a coating method.

SUMMARY OF THE INVENTION

An object of the invention is to provide metal complexes of halogen-substituted o-benzenedithiols having a high compatibility with resins which complexes are not crystallized from the resins even if the concentration thereof is increased.

Another object of the invention is to provide intermediate halogen-substituted o-benzenedithiols and a process for producing the same.

Still another object of the invention is to provide plastic compositions containing the metal complexes of halogen-substituted o-benzenedithiols as near-infrared absorbers.

According to the present invention, metal complexes of halogen-substituted benzenedithiols of the general formula (I):

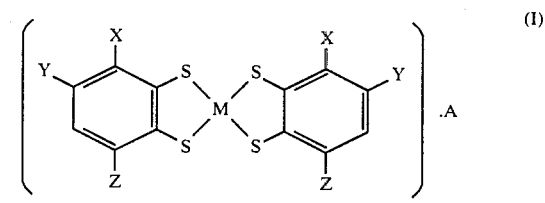

wherein X represents a chlorine or bromine atom, Y and Z represent each a hydrogen or chlorine atom when X is a chlorine atom or they represent each a hydrogen or bromine atom when X is a bromine atom, M represents a nickel, palladium or platinum atom, and A represents a quaternary ammonium group, are provided.

The metal complexes of halogen-substituted o-benzenedithiols of the present invention have a high compatibility with resins. Even if the concentration of the metal complexes in the resins is increased, they are not crystallized out of the resins during the use for a long time.

The above-mentioned metal complexes are produced from halogen-substituted o-benzenedithiols of the general formula (II):

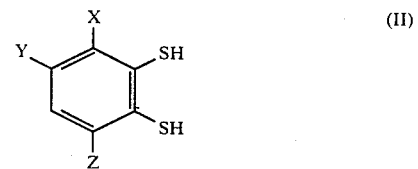

wherein X represents a chlorine or bromine atom, and Y and Z represent each a hydrogen or chlorine atom when X is a chlorine atom or they represent each a hydrogen or bromine atom when X is a bromine atom. They are also new compounds.

DETAILED DESCRIPTION OF THE INVENTION

The metal complexes of the above general formula (I) include, for example, bis(1,2,4-trichloro-5,6-dithiophenolato)nickel-tetra-n-butylammonium, bis(1,4-dichloro-5,6-dithiophenolato)nickel-tetra-n-butylammonium, bis(1-chloro-5,6-dithiophenolato)nickel-tetra-n-butylammonium and corresponding metal complexes containing palladium or platinum in place of nickel or containing tetra-n-propylammonium group or trioctylmethylammonium group in place of the quaternary tetra-n-butylammonium group; as well as bis(1,2,4-tribromo-5,6-dithiophenolato)nickel-tetra-n-butylammonium, bis(1,4-dibromo-5,6-dithiophenolato)nickel-tetra-n-butylammonium, bis(1-bromo-5,6-dithiophenolato)nickel-tetra-n-butylammonium and corresponding metal complexes containing palladium or platinum in place of nickel or containing tetra-n-propylammonium group or trioctylmethylammonium group in place of the quaternary tetra-n-butylammonium group.

As compared with known metal complexes of tetrachlorobenzenedithiol, the metal complexes of the present invention have a higher compatibility with resins. For example, they have a compatibility with acrylic resin of at least 20 Wt. %. Even if the concentration of them in the resins is increased, they are not crystallized out of the resins during the use for a long time.

As the halogen-substituted o-benzenedithiols of general formula (II) used as the starting materials for the metal complexes of general formula (I), there may be mentioned, for example, 1,2,4-trichlorobenzene-5,6-dithiol, 1,4-dichlorobenzene-5,6-dithiol, 1-chlorobenzene-5,6-dithiol, 1,2,4-tribromobenzene-5,6-dithiol, 1,4-dibromobenzene-5,6-dithiol and 1-bromobenzene-5,6-dithiol.

The new halogen-substituted o-benzenedithiols of the present invention cannot be synthesized by a known process for producing 1,2,3,4-tetrachlorobenzene-5,6-dithiol from hexachlorobenzene, i.e., a process disclosed in the above described "Journal of the American Society" Vol. 88 wherein hexachlorobenzene is reacted with sodium hydrosulfide under heating to 145° C. in the presence of iron powder in dimethylformamide as a solvent to form tetrachlorobenzenedithiol.

The inventors have found that intended halogen-substituted o-benzenedithiols can be obtained from pentahalogenated benzenes or lower-halogenated benzenes by adding sulfur to the starting materials in the presence of iron powder or an iron salt under the above-mentioned reaction conditions. By this process, for example, 1,2,4-trichlorobenzene-5,6-dithiol, 1,4-dichlorobenzene-5,6-dithiol, 1-chlorobenzene-5,6-dithiol, 1,2,4-tribromobenzene-5,6-dithiol, 1,4-dibromobenzene-5,6-dithiol and 1-bromobenzene-5,6-dithiol can be obtained from corresponding pentachlorobenzene, 1,2,3,4-tetrachlorobenzene, 1,2,3-trichlorobenzene, pentabromobenzene, 1,2,3,4-tetrabromobenzene and 1,2,3-tribromobenzene.

The compounds of general formula (II) are produced by reacting polyhalogenated benzenes of general formula (III):

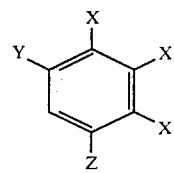

wherein X, Y and Z have the same meaning as above, with hydrosulfides under heating in the presence of sulfur and iron powder or an iron salt in a polar organic solvent. The mechanism of the development of the effects of sulfur used in this process has not fully been elucidated. It is supposed, however, from the experimental fact that at least 5 wt. %, based on the hydrosulfide, of sulfur is required for sufficiently improving the yield of the halogen-substituted o-benzenedithiols, that sulfur exhibits no appreciable catalytic effect during the reaction. Instead, a polysulfide is formed from sulfur and the hydrosulfide, which polysulfide attacks the halogen-substituted o-benzenemonothiol formed from the polyhalogenated benzene to accelerate the formation of halogen-substituted o-benzenedithiol.

As the polyhalogenated benzenes of the above general formula (III), there may be mentioned pentachlorobenzene, 1,2,3,4-tetrachlorobenzene, 1,2,3-trichlorobenzene, pentabromobenzene, 1,2,3,4-tetrabromobenzene and 1,2,3-tribromobenzene.

As the hydrosulfides, there may be mentioned alkali metal or alkaline earth metal hydrosulfides. Among them, sodium hydrosulfide or potassium hydrosulfide is used preferably.

The molar ratio of the polyhalogenated benzene to the hydrosulfide is 1:2-5, preferably 1:2.5-3.0.

As the polar organic solvents used in the above-mentioned process, alcohols or amides are preferred. Preferred alcohols include methanol, ethanol, n-propanol, isopropanol, n-butanol and tert-butanol. As the amide solvents, there may be used dimethylformamide, diethylformamide, dimethylacetamide, N-methylpyrrolidone, tetramethylurea and hexamethylphosphoramide. The amount of the polar organic solvent is 1 to 10 parts by weight, preferably 2 to 5 parts by weight, per part by weight of the polyhalogenated benzene.

As the iron powder or iron salts used, there may be mentioned iron powder and, divalent or trivalent iron salts such as iron chloride, iron bromide, iron nitrate and iron phosphate. The molar ratio of the iron powder or iron salt to the polyhalogenated benzene is 0.25-2.0:1, preferably 0.5-1.0:1.

The amount of sulfur used is 3 to 30 wt. %, preferably 5 to 15 wt. %, based on the hydrosulfide. If the amount of sulfur is insufficient, the intended halogen-substituted o-benzenedithiol cannot be formed or the yield is reduced seriously. If the amount of sulfur is excessive, sulfur is easily liberated during the after-treatment after completion of the reaction unfavorably.

The reaction temperature is 110° to 145° C., preferably 120° to 140° C. The reaction time which varies depending on the reaction solvent, hydrosulfide and amount of sulfur is generally 8 to 16 h.

After carrying out the reaction under the above-mentioned conditions, the reaction mixture is cooled, water is added thereto and the mixture is filtered. A black solid thus obtained is heated together with zinc oxide in the presence of an alkali. After the filtration, a mineral acid is added to the filtrate obtained and the intended halogen-substituted o-benzenedithiol thus liberated is taken.

The obtained, new halogen-substituted o-benzenedithiol has a capacity of chelating metals to form new metal complexes of halogen-substituted o-benzenedithiol.

The metal complexes of general formula (I) are obtained by reacting the compounds of general formula (II) with salts of nickel, palladium or platinum in a polar solvent and then reacting the reaction product with tetraalkylammonium salts.

In a preferred mode of emobidment, 1 mol of the compound of general formula (II) is dissolved or dispersed in a proper polar solvent, 0.5 atom equivalent (as metal) of a metal salt capable of yielding nickel, palladium or platinum ion such as nickel chloride, palladium chloride or potassium chloroplatinate is added to the reaction liquid under stirring at ambient temperature, and stirring is continued to form a metal complex of halogen-substituted o-benzenedithiol. Thereafter, 0.5 to 1.0 mol of a quaternary ammonium halide such as tetra-n-butylammonium bromide, tetra-n-propylammonium bromide, trioctylmethylammonium bromide, tetra-n-butylammonium chloride, tetra-n-propylammonium chloride or trioctylmethylammonium chloride, or 0.5 to 1.0 mol of a quaternary ammonium hydroxide obtained by reacting a quaternary ammonium halide with an alkali such as sodium hydroxide in equimolar amounts is added to the reaction liquid and stirring is continued. Thus, an intended metal complex of halogen-substituted o-benzenediol is obtained.

As the polar solvent, there may be used, for example, tetrahydrofuran, methanol, ethanol or isopropanol.

The metal complexes of halogen-substituted o-benzenedithiols of the present invention have excellent near-infrared absorbing capacity, thermal stability and weather resistance equivalent to those of known metal complexes of tetrachlorobenzenedithiols. In addition, they have a high compatibility with plastics which cannot be expected in the metal complexes of tetrachlorobenzenedithiols. Therefore, the metal complexes of the present invention can be incorporated in plastics in high concentrations as near-infrared absorbers and they are not crystallized out of the plastics during the use for a long time.

Therefore, by incorporating the metal complexes of the present invention in resins for various purposes, it becomes possible to increase the near-infrared absorbance per unit thickness of the resins, whereas the absorbance was limited when conventional metal complexes of tetrachlorobenzenedithiols are used. Accordingly, the uses of the resins are broadened. They can be used not only for the production of articles having a relatively high thickness such as optical filters of photodiodes and agricultural films used for the selective absorption of the sunlight but also for the production of thin films having high absorbances such as those used for sunglass coating and laser heat mode recording.

Thus, the present invention provides also near-infrared absorbing plastic compositions characterized by containing the metal complexes of general formula (I) as near-infrared absorbers.

As the starting materials for the plastic compositions, there may be used all sorts of plastics having excellent transparency and mechanical properties. They include, for example, polyesters such as polyethylene terephthalate, cellulose esters such as nitrocellulose and cellulose triacetate, polyolefins such as polyethylene and polypropylene, polyacrylic resins such as polymethyl acrylate and polymethyl methacrylate, polyvinyls such as polyvinyl chloride, polyvinylidene chloride, vinyl chloride/vinyl acetate copolymer and polystyrene, and polycarbonates. The plastics are selected so as to meet the purpose for which the near-infrared absorbing capacity is required.

The amount of the metal complexes of the present invention to be incorporated in the plastics varies depending on the type and thickness of the plastics, desired absorbance and the type of the metal complex, though it is in general within the range of 0.1 to 99% by weight.

As processes for obtaining moldings of the near-infrared absorbing plastic compositions according to the present invention, there may be mentioned, for example, a process wherein the metal comples is incorporated in the plastic in the course of molding the same, or more particularly, the metal complex is mixed with the plastic powder or pellets and the mixture is fused and subjected to the compression or extrusion molding to obtain plastic moldings of a desired shape, and a process wherein a polymer solution or dispersion containing the metal complex is applied to the surface of a substrate to which near-infrared absorbing power is to be imparted to form a near-infrared absorbing layer. In these processes, if necessary, a stabilizer, plasticizer, antioxidant and U.V. absorber may also be used.

Thus, in the plastic compositions of the present invention, it has become possible to incorporate the metal complexes in a high concentration as a near-infrared absorber in a plastic. These plastic compositions may be used for the production of agricultural films used for the selective absorption of the sunlight, sunglasses and welder's glasses used for keeping from the glare of the light or for preventing the fatigue of eyeballs, aircraft windows and TV filters, optical filters for the compensation of wavelength dependence of the sensitivity of optical transducer elements such as photodiodes and light-emitting diodes and heat mode recording media of semiconductor laser beams having oscillation wavelengths in a near-infrared zone.

Melting points and absorption characteristics of typical metal complexes of general formula (I) are shown in Table 1.

It is to be noted, however, that the metal complexes of the present invention are not limited to those shown in Table 1.

TABLE 1

| No. | Structural formula | M.P. °C. | Maximum absorption wavelength $\lambda_{max}$ nm | Molar extinction coefficient $mol^{-1} cm^{-1}$ |
|---|---|---|---|---|
| 1 | [Ni complex with tetrachlorobenzenedithiolate ligands] · $N(n\text{-}C_4H_9)_4$ | 138~140 | 870 | 14900 |
| 2 | [Pd complex with tetrachlorobenzenedithiolate ligands] · $N(n\text{-}C_4H_9)_4$ | 141~143 | 1140 | 11500 |
| 3 | [Pt complex with tetrachlorobenzenedithiolate ligands] · $N(n\text{-}C_4H_9)_4$ | 146~147 | 890 | 22500 |
| 4 | [Ni complex with trichlorobenzenedithiolate ligands] · $N(n\text{-}C_4H_9)_4$ | 204~205 | 855 | 14800 |
| 5 | [Ni complex with trichlorobenzenedithiolate ligands] · $N(C_8H_{17})_3CH_3$ | 102~105 | 855 | 14000 |
| 6 | [Ni complex with dichlorobenzenedithiolate ligands] · $N(n\text{-}C_4H_9)_4$ | 125~127 | 860 | 15400 |
| 7 | [Ni complex with tetrabromobenzenedithiolate ligands] · $N(n\text{-}C_4H_9)_4$ | 193~196 | 900 | 10500 |

The following examples will further illustrate the present invention. Parts in the examples are given by weight.

EXAMPLE 1

50 parts of pentachlorobenzene, 38 parts of 70% sodium hydrosulfide, 4 parts of sulfur and 6 parts of iron powder were added to 150 parts of N,N-dimethylformamide. The mixture was heated to 135° C. for 10 h while nitrogen gas was introduced therein slowly to carry out the reaction. The reaction mixture was cooled. After adding 500 parts of water, the mixture was filtered to obtain a black filter cake. The whole amount of the filter cake was air-dried and then added to 250 parts of methanol together with a solution of 20 parts of zinc oxide and 50 parts of sodium hydroxide in 250 parts of water. The whole mixture was heated to a reflux temperature of methanol for 1 h. After cooling, the mixture was filtered and the filtrate was poured in a mixture of 500 parts of water and 250 parts of 98% sulfuric acid to precipitate a light yellow powder. After the filtration followed by air-drying, 39 parts of a light yellow crystal (m.p. 95°–110° C.) was obtained. The crystal was recrystallized from chloroform to obtain 37 parts of 1,2,4-trichlorobenzene-5,6-dithiol in the form of light yellow needle-like crystal (yield: 75 molar %).

Melting point: 115°–116° C.

| Elementary analysis: | C (%) | H (%) | Cl (%) | S (%) |
|---|---|---|---|---|
| calculated (as $C_6H_3Cl_3S_2$): | 29.34 | 1.23 | 43.31 | 26.11 |
| found: | 29.28 | 1.28 | 43.17 | 26.31 |

NMR $\delta CDCl_3$: 4.65(2H,d), 7.34(1H,S).

EXAMPLE 2

43 parts of 1,2,3,4-tetrachlorobenzene, 35 parts of 70% sodium hydrosulfide, 3 parts of sulfur and 15 parts of ferrous chloride tetrahydrate were added to 210 parts of N,N-diethylformamide. The mixture was heated to 140° C. for 10 h while nitrogen gas was introduced therein slowly to carry out the reaction. The reaction mixture was cooled. After adding 500 parts of water, the mixture was filtered to obtain a black filter cake. The filter cake was air-dried and then added to 250 parts of methanol together with a solution of 20 parts of zinc oxide and 50 parts of sodium hydroxide in 250 parts of water. The whole mixture was heated to a reflux temperature of methanol for 1 h. After cooling, the mixture was filtered and the filtrate was poured in a mixture of 500 parts of water and 250 parts of 98% sulfuric acid to precipitate a light yellow powder. After the filtration followed by air-drying, 32 parts of a light yellow crystal (m.p. 47°–57° C.) was obtained. The crystal was recrystallized from chloroform to obtain 28 parts of 1,4-dichlorobenzene-5,6-dithiol in the form of light yellow needle-like crystal (yield: 67 molar %).

Melting point: 57°–58° C.

| Elementary analysis: | C (%) | H (%) | Cl (%) | S (%) |
|---|---|---|---|---|
| calculated (as $C_6H_4Cl_2S_2$): | 34.13 | 1.91 | 33.59 | 30.37 |
| found: | 33.78 | 1.95 | 33.33 | 30.51 |

NMR $\delta CDCl_3$: 4.58(2H,S), 7.52(1H,S).

EXAMPLE 3

100 parts of methanol, 18.2 parts of 1,2,3-trichlorobenzene, 510 parts of 35% potassium hydrosulfide, 2 parts of sulfur and 8.5 parts of ferrous phosphate octahydrate were charged in a glass vessel. The glass vessel was placed in a stainless steel autoclave and the reaction was carried out at 135° C. for 12 h. After cooling, the glass vessel was taken out and the reaction liquid was added to 300 parts of water. A black solid thus formed was filtered out and air-dried. The whole quantity of the solid was added to 125 parts of methanol together with a solution of 10 parts of zinc oxide and 25 parts of sodium hydroxide in 125 parts of water. The whole mixture was heated to a reflux temperature of methanol for 1 h. After cooling, the mixture was filtered and the filtrate was poured in a mixture of 250 parts of water and 125 parts of 98% sulfuric acid to form an oily layer. The oily product was extracted with 300 parts of benzene and then concentrated to obtain a colorless semi-solid. The semi-solid was distilled under reduced pressure and a fraction of 108°–110° C./1 mmHg was collected to obtain 8.5 parts of 1-chlorobenzene-5,6-dithiol in the form of a colorless semi-solid (yield: 48 molar %).

| Elementary analysis: | C (%) | H (%) | Cl (%) | S (%) |
|---|---|---|---|---|
| calculated (as $C_6H_5ClS_2$): | 40.79 | 2.85 | 20.07 | 36.30 |
| found: | 40.37 | 2.91 | 20.23 | 36.75 |

NMR $\delta CDCl_3$: 4.70(2H,d), 7.62~6.98(3H,m).

EXAMPLE 4

The reaction was carried out in the same manner as in Example 1 except that 150 parts of N,N-dimethylformamide was replaced with 250 parts thereof and that 50 parts of pentachlorobenzene was replaced with 95 parts of pentabromobenzene. After cooling followed by addition of 500 parts of water and filtration, a dark brown solid was obtained.

After the same treatment as in Example 1, 33 parts of 1,2,4-tribromobenzene-5,6-dithiol was obtained in the form of a yellow needle-like crystals (yield: 43 molar %).

Melting point: 125°–127° C.

| Elementary analysis: | C (%) | H (%) | Cl (%) | S (%) |
|---|---|---|---|---|
| calculated (as $C_6H_3Br_3S_2$): | 24.10 | 1.01 | 53.45 | 21.44 |
| found: | 23.98 | 1.13 | 52.11 | 21.82 |

NMR $\delta CDCl_3$: 4.72(2H,d), 7.20(1H,S).

COMPARATIVE EXAMPLE 1

The reaction was carried out in the same manner as in Example 1 except that the addition of 4 parts of sulfur was omitted. After cooling followed by addition of 500 parts of water and filtration, a dark solid containing a white crystal was obtained.

After the same after-treatment as in Example 1, 42 parts of 1,2,4,5-tetrachlorobenzene-6-thiol was obtained in the form of a colorless needle-like crystal (yield: 84 molar %).

Melting point: 109°–111° C.

| Elementary analysis: | C (%) | H (%) | Cl (%) | S (%) |
|---|---|---|---|---|
| calculated (as $C_6H_2Cl_4S$): | 29.34 | 0.70 | 57.21 | 12.88 |
| found: | 29.25 | 0.79 | 56.82 | 12.96 |

EXAMPLE 5

9.0 parts of 1,2,4-trichlorobenzene-5,6-dithiol was dissolved in 500 parts of tetrahydrofuran. A solution of 4.2 parts of nickel chloride hexahydrate in 50 parts of ethanol was added to the former solution to change the color thereof into dark green. Then, 6.0 parts of tetra-n-butylammonium bromide was added thereto and the mixture was stirred for 2 h. The reaction liquid was distilled under reduced pressure to concentrate the same into a volume of about 1/3. The product was recrystallized from a mixture of dichloromethane and methanol in a weight ratio of 1:3 to obtain 11.5 parts of bis(1,2,4-trichloro-5,6-dithiophenolato)nickel-tetra-n-butylammonium (yield: 80 molar %).

Melting point: 138°–140° C.

| Elementary analysis: | C (%) | H (%) | N (%) | Cl (%) | S (%) |
|---|---|---|---|---|---|
| calculated (as $C_{28}H_{38}NCl_6S_4Ni$): | 42.66 | 4.86 | 1.78 | 26.99 | 16.27 |
| found: | 42.59 | 4.92 | 1.72 | 27.52 | 16.77 |

EXAMPLE 6

22 parts of 1,4-dichlorobenzene-5,6-dithiol was suspended in 800 parts of methanol. A solution of 12.4 parts of nickel chloride hexahydrate in 100 parts of methanol was added to the suspension under stirring to change the color thereof into dark green.

Then, 18.3 parts of tetra-n-butylammonium bromide was added thereto and the mixture was stirred for 2 h. The reaction liquid was distilled under reduced pressure into a volume of about 1/5. After the filtration, 31 parts of a green solid was obtained. The product was recrystallized from a mixture of dichloromethane and methanol in a weight ratio of 1:1 to obtain 26 parts of bis(1,4-dichloro-5,6-dithiophenolato)nickle-tetra-n-butylammonium (yield: 70 molar %).

Melting point: 204°–205° C.

| Elementary analysis: | C (%) | H (%) | N (%) | Cl (%) | S (%) |
|---|---|---|---|---|---|
| calculated (as $C_{28}H_{40}NCl_4S_4Ni$) | 46.75 | 5.60 | 1.95 | 19.71 | 17.83 |
| found: | 46.25 | 5.73 | 1.89 | 19.88 | 18.01 |

EXAMPLE 7

The same procedure as in Example 6 was repeated except that 22 parts of 1,4-dichlorobenzene-5,6-dithiol was replaced with 18.5 parts of 1-chlorobenzene-5,6-dithiol to obtain 26 parts of bis(1-chloro-5,6-dithiophenolato)nickel-tetra-n-butylammonium (yield: 77 molar %).

Melting point: 125°–127° C.

| Elementary analysis: | C (%) | H (%) | N (%) | Cl (%) | S (%) |
|---|---|---|---|---|---|
| calculated (as $C_{28}H_{42}NCl_2S_4Ni$): | 51.70 | 6.51 | 2.15 | 10.90 | 19.72 |
| found: | 51.55 | 6.67 | 2.13 | 11.02 | 20.10 |

EXAMPLE 8

The same procedure as in Example 5 was repeated except that 4.2 parts of nickel chloride hexahydrate was replaced with 7.3 parts of potassium chloroplatinate to obtain 13 parts of bis(1,2,4-trichloro-5,6-dithiophenolato)platinum-tetra-n-butylammonium (yield: 80 molar %).

Melting point: 146°–147° C.

| Elementary analysis: | C (%) | H (%) | N (%) | Cl (%) | S (%) |
|---|---|---|---|---|---|
| calculated (as $C_{28}H_{38}NCl_6S_4Pt$): | 36.37 | 4.14 | 1.51 | 23.01 | 13.87 |
| found: | 36.40 | 4.18 | 1.49 | 22.98 | 13.96 |

EXAMPLE 9

The same procedure as in Example 5 was repeated except that 9.0 parts of 1,2,4-trichlorobenzene-5,6-dithiol was replaced with 13.3 parts of 1,2,4-tribromo-benzene-5,6-dithiol to obtain 14 parts of bis(1,2,4-tribromo-5,6-dithiophenolato)nickel-tetra-n-butylammonium (yield: 73 molar %).

Melting point: 193°–196° C.

| Elementary analysis: | C (%) | H (%) | N (%) | BR (%) | S (%) |
|---|---|---|---|---|---|
| calculated (as $C_{28}H_{38}NBr_6S_4Ni$): | 31.88 | 3.63 | 1.33 | 45.44 | 12.16 |
| found: | 31.75 | 3.69 | 1.29 | 44.38 | 12.22 |

EXAMPLE 10

10 parts of polymethyl acrylate was added to a solvent mixture of 45 parts of acetone and 45 parts of toluene. 3 parts of the metal complex of halogen-substituted benzenedithiol obtained in any of Examples 5 to 9 or, for comparison, known bis(1,2,3,4-tetrachloro-5,6-dithiophenolato)nickel-tetra-n-butylammonium was added to the former mixture to obtain a solution. The solution was applied to the surface of a polyvinyl chloride film having a thickness of 0.2 mm by means of a samll gravure coater to form a coating film having a thickness after drying of 782 . The film was dried with hot air at 70° C. The film was left to stand in a constant temperature bath at 60° C. for 7 days and observed by means of a microscope. It was recognized that fine needle-like crystals were scattered in the film containing bis(1,2,3,4-tetrachloro-5,6-dithiophenolato)nickel-tetra-n-butylammonium, while no crystal was observed at all in the films containing halogen-substituted benzenedithiols obtained in Examples 5 to 9.

EXAMPLE 11

A solution of 3 parts of the metal complex of halogen-substituted benzenedithiol obtained in any of Examples 5 to 9 or, for comparison, known bis(1,2,3,4-tetrachloro-5,6-dithiophenolato)nickel-tetra-n-butylammonium and 5 parts of nitrocellulose in 50 parts of methyl ethyl ketone was applied to a polyethylene terephthalate film by means of a spinner and dried under a given condition to form a coating film of about 1 μm. The film was left to stand in a constant temperature bath at 60° C. for 7 days and the test pieces were observed by means of an optical microscope. No crystal was observed at all in the films containing the metal complexes of halogen-substituted benzenedithiol obtained in Examples 5 to 9, while fine needle-like crystals were scattered in the film containing bis(1,2,3,4-tetrachloro-5,6-dithiophenolato)-nickel-tetra-n-butylammonium.

REFERENTIAL EXAMPLE 1

(Effects of Intercepting Infrared Rays)

A film containing bis(1,2,4-trichloro-5,6-dithiophenolato)nickel-tetra-n-butylammonium (hereinafter referred to as film A) obtained in Example 10 was spread over the sides and the top of a wood frame having a size of 90 cm length, 120 m width and 90 cm height. An illuminometer (Toshiba No. 5 Illuminometer), Gortzinski heliograph and integrating illuminometer (PH-11; a product of Toyo Rika Kogyo) were placed therein. The illuminance (lux), quantity of sunshine (cal) and radiant quantities (mW.min/cm$^2$) in ultraviolet, visible and infrared regions were determined and the results were shown by relative values to values (100) obtained without using the film (in the open air).

The results are shown in Table 2. The film A of the present invention exhibited an effect of reducing the quantity of sunshine to about ½ while the quantity of light in the visible region was reduced by only 22%.

TABLE 2

| | Illuminance, quantity of sunshine and radiant quantity (relative values) | | | | |
|---|---|---|---|---|---|
| | Illuminance | Quantity of sunshine | Radiant quantity | | |
| | | | U.V. | Visible | I.R. |
| Open air | 100 | 100 | 100 | 100 | 100 |
| Transparent film (see Note) | 100 | 84 | 43 | 82 | 86 |
| Film A | 78 | 58 | 21 | 78 | 48 |

Note
A control film prepared in the same manner as in Example 10 except that no metal complex was used.

REFERENTIAL EXAMPLE 2

The surface of a film coated with bis(1,4-dichloro-5,6-dithiophenolato)nickel-tetra-n-butylammonium (hereinafter referred to as film B) obtained in Example 11 was sweeped linearly by focussed semiconductor laser beams (GaAlAs laser, 830 nm, 5 mW output). The part irradiated with the laser beams was observed by means of an electron microscope. The trajectory of the laser beams was quite clear. In the observation by means of an optical microscope, it was recognized that the irradiated part was colored in yellow, while the non-irradiated part was green. It was proved that the laser beem recording was possible by using film B.

EXAMPLE 12

A mixture of 0.15 part of bis(1-chloro-5,6-dithiophenolato)nickel-tetra-n-butylammonium and 100 parts of polymethyl methacrylate was compression-molded at a press temperature of 150° C. under a press pressure of 280 kg/cm$^2$ to form test pieces having a thickness of 1.0 mm. The test pieces were green. The maximum percent transmission in the visible region of 350 to 1100 nm was at least 70%. Percent transmission at below 400 nm or in the range of 800 to 950 nm was less than 10%. Thus, an optical filter having spectral properties close to the visual sensitivity was obtained.

What is claimed is:

1. Metal complexes of halogen-substituted o-benzenedithiols of general formula (I):

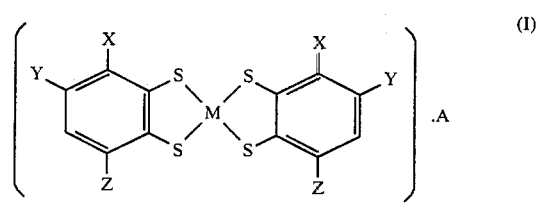

wherein X represents a chlorine or bromine atom, Y and Z represent each a hydrogen or chlorine atom when X is a chlorine atom or they represent each a hydrogen or bromine atom when X is a bromine atom, M represents a nickel, palladium or platinum atom, and A represents a quaternary ammonium group selected from the group consisting of tetra-n-butyl-ammonium, tetra-n-propylammonium and trioctylmethylammonium.

2. Metal complexes of halogen-substituted o-benzenedithiols according to claim 1 which are alkylammonium salts of complexes of a metal, selected from the group nickel, palladium or platinum, of bis(1,2,4-trichloro-5,6-dithiophenolate), bis(1,4-dichloro-5,6-dithiophenolate), bis(1-chloro-5,6-dithiophenolate), bis(1,2,4-tribromo-5,6-dithiophenolate), bis(1,4-dibromo-5,6-dithiophenolate) or bis(1-bromo-5,6-dithiophenolate).

* * * * *

UNITED STATES PATENT AND TRADEMARK OFFICE
CERTIFICATE OF CORRECTION

PATENT NO. : 4,508,655
DATED : April 2, 1985
INVENTOR(S) : Katsuyoshi Sasagawa & Masao Imai It is certified that error appears in the above-identified patent and that said Letters Patent are hereby corrected as shown below:

Col. 1, line 26; - "for" should read -- für --

Col. 12, line 41; - "782" should read -- 7 µ --

Col. 14, line 4 of Claim 2; - between the words "group" and "nickel" insert -- consisting of --

Signed and Sealed this

Twentieth Day of August 1985

[SEAL]

Attest:

DONALD J. QUIGG

Attesting Officer

Acting Commissioner of Patents and Trademarks